United States Patent [19]

DeGuchi et al.

[11] Patent Number: 5,693,193
[45] Date of Patent: Dec. 2, 1997

[54] PROCESS FOR RECOVERING PROPYLENE OXIDE

[75] Inventors: Takashi DeGuchi, Niihama; Kazuo Kimura, Ichihara; Naoto Meki; Masaru Ishino, both of Ichihara; Tetsuya Suzuta, Takatsuki, all of Japan

[73] Assignee: Sumitomo Chemical Company, Limited, Osaka, Japan

[21] Appl. No.: 409,058

[22] Filed: Mar. 23, 1995

[30] Foreign Application Priority Data

| Mar. 24, 1994 | [JP] | Japan | 6-053726 |
| May 20, 1994 | [JP] | Japan | 6-106655 |
| Aug. 10, 1994 | [JP] | Japan | 6-188414 |
| Dec. 16, 1994 | [JP] | Japan | 6-313223 |

[51] Int. Cl.$^6$ ............................ B01D 3/34; C07D 301/32
[52] U.S. Cl. ........................ 203/51; 203/54; 203/55; 203/56; 203/58; 203/60; 203/62; 203/63; 203/64; 549/541
[58] Field of Search ................... 203/58–59, 63, 203/60, 68–70, 67, 62, 51, 54, 91, 57, 64, 1, 55–56; 549/541

[56] References Cited

U.S. PATENT DOCUMENTS

| 3,350,422 | 10/1967 | Kollar . | |
| 3,351,635 | 11/1967 | Kollar . | |
| 3,459,810 | 8/1969 | Choo et al. . | |
| 3,578,568 | 5/1971 | Washall | 203/64 |
| 3,632,482 | 1/1972 | Hoory et al. | 203/63 |
| 3,715,284 | 2/1973 | Burns et al. | 203/56 |
| 4,369,096 | 1/1983 | Seifert et al. | 203/58 |
| 4,691,035 | 9/1987 | Sanderson et al. . | |
| 4,971,661 | 11/1990 | Meyer et al. | 203/54 |
| 4,977,285 | 12/1990 | Marquis et al. . | |
| 5,006,206 | 4/1991 | Shih et al. . | |
| 5,116,466 | 5/1992 | Marquis et al. . | |
| 5,127,997 | 7/1992 | Smith et al. | 203/81 |
| 5,129,996 | 7/1992 | Shih | 203/64 |
| 5,139,622 | 8/1992 | Marquis et al. . | |
| 5,145,563 | 9/1992 | Culbreth, III et al. | 203/14 |
| 5,154,803 | 10/1992 | Marquis et al. . | |
| 5,154,804 | 10/1992 | Marquis et al. | 203/63 |
| 5,160,587 | 11/1992 | Marquis et al. . | |
| 5,262,017 | 11/1993 | Moyer et al. . | |
| 5,340,446 | 8/1994 | Nelson et al. | 203/64 |
| 5,354,430 | 10/1994 | Culbreth, III et al. . | |
| 5,354,431 | 10/1994 | Taylor . | |

FOREIGN PATENT DOCUMENTS

| 880337 | 9/1971 | Canada | 260/348.22 |
| 0004019 | 9/1979 | European Pat. Off. . | |
| 0061393 | 9/1982 | European Pat. Off. . | |
| 0389300 | 9/1990 | European Pat. Off. . | |
| 0410600 | 1/1991 | European Pat. Off. . | |
| 0457421 | 11/1991 | European Pat. Off. . | |
| 0566356 | 10/1993 | European Pat. Off. . | |
| 2018290 | 5/1970 | France . | |
| 681866 | 9/1939 | Germany . | |
| 1224293 | 1/1969 | Germany . | |
| 1568808 | 4/1970 | Germany . | |
| 1568836 | 7/1970 | Germany . | |
| 1668232 | 9/1971 | Germany . | |
| 2810662 | 9/1979 | Germany . | |
| 1138620 | 1/1969 | United Kingdom . | |

*Primary Examiner*—Virginia Manoharan
*Attorney, Agent, or Firm*—Sughrue, Mion, Zinn, Macpeak & Seas, PLLC

[57] ABSTRACT

Propylene oxide is recovered through the use of an additive in a distillation solution, resulting in suppressed side reactions and reduced loss of product. Propylene oxide is produced by oxidizing ethylbenzene in a liquid phase with molecular oxygen to a obtain a reaction liquid containing ethylbenzene hydroperoxide; distilling the reaction liquid to obtain a concentrated solution of ethylbenzene hydroperoxide; further mixing and reacting the concentrated solution with propylene to obtain a mixed solution containing propylene oxide; and distilling the mixed solution to separate and recover propylene oxide. At least one compound selected from aliphatic saturated alcohols having 2 to 4 carbon atoms, allyl alcohol, saturated aliphatic hydrocarbons having 6 or 7 carbon atoms, benzene, ethers, ketones, nitriles, amines, pyridines, diamines, and aminoalcohols is added to the mixed distillation solution in an amount of 0.01–100 parts by weight per 100 parts by weight of propylene oxide.

6 Claims, No Drawings

PROCESS FOR RECOVERING PROPYLENE OXIDE

FIELD OF THE INVENTION

The present invention relates to a process for recovering propylene oxide.

BACKGROUND OF THE INVENTION

Propylene oxide is one of useful industrial chemicals used as a material for producing polyurethanes and for other uses. It is extensively produced by a process comprising the steps of oxidizing ethylbenzene in a liquid phase with molecular oxygen to obtain a reaction liquid containing ethylbenzene hydroperoxide, then distilling the reaction liquid to obtain a concentrated solution of ethylbenzene hydroperoxide, and further mixing and reacting the concentrated solution with propylene.

Propylene oxide can be recovered by distilling the mixed solution containing propylene oxide. However, this method of recovery involves a number of problems. Since the mixed solution containing propylene oxide obtained by reacting ethylbenzene hydroperoxide with propylene usually contains about 0.01–0.5% by weight of water, when the solution is distilled to recover propylene oxide a side reaction of propylene oxide with water takes place to form propylene glycol, resulting in increased loss of propylene oxide (hereinafter sometimes abbreviated as PO). Further, the mixed solution contains a small amount of phenol and ethylphenols. These phenols also react with PO during distillation to increase the loss of PO. When the solution further contains organic acids or molybdic acid, the loss of PO remarkably increases. Therefore, the development of a process for recovering PO with decreased loss of PO has been desired.

For recovering propylene oxide from a mixed solution containing propylene oxide, the following processes have already been known.

U.S. Pat. No. 3,715,284 discloses a process in which, in synthesizing propylene oxide from propylene and oxygen and recovering propylene oxide from the reaction liquid, the reaction liquid is distilled in the presence of acetone or a mixture of acetone and methanol added thereto. However, this process needs to use acetone or the mixture of acetone and methanol in an amount of 4 times or more by weight of the amount of propylene oxide, and requires a great deal of energy for separation of propylene oxide from the additive because their boiling points are close to each other. In this process, moreover, the column bottom temperature of the distillation column must be 123° C. or below because too high bottom temperature increases the loss of PO; however, in producing propylene oxide from ethylbenzene hydroperoxide and propylene, the boiling point of ethylbenzene commonly used as the solvent is 136° C. at 1 atm and the boiling point of methylbenzyl alcohol, which is another reaction product, is 200° C. or more at 1 atm, therefore the distillation must be conducted at reduced pressure which results in economical disadvantage such large cooling energy for PO vapor.

French Pat. No. 2018290 discloses a process in which, in synthesizing propylene oxide by epoxidation of propylene using peracetic acid and recovering propylene oxide from the resulting reaction mixture, the reaction mixture is distilled in the presence of esters, such as an acetic ester, added thereto. In general, however, esters tend to be readily hydrolyzed and the resulting organic acids cause side reactions which will promote the loss of propylene oxide. Further, the esters must be added in about the same amount by mole as that of propylene oxide to be separated by distillation. Thus, the process is not sufficiently efficient.

JP-A-54-4923 discloses a method that distillation is conducted in the presence of a tri(lower alkyl)phosphate. In this method, however, since the tri(lower alkyl)phosphate is present in the reboiler during distillation, the operating temperature of the reboiler must be not higher than the decomposition temperature of the tri(lower alkyl)phosphate. Moreover, since the tri(lower alkyl)phosphate is recycled in the form of reboiler mixed liquid, it cannot be separated and recovered by distillation or other means; and since the reboiler liquid is recycled together with the column bottom liquid, this method cannot be favorably applied to a process wherein styrene monomer is simultaneously produced by dehydrating the column bottom liquid at a later step, as in the production of propylene oxide from ethylbenzene hydroperoxide and propylene.

SUMMARY OF THE INVENTION

Thus, the additives hitherto used in recovering propylene oxide by distillation have various drawbacks and are not suitable for attaining the object of the present invention. Therefore, the present inventors have made extensive study to develop a process for efficiently recovering propylene oxide by suppressing side reactions to lower the loss of propylene oxide. As the result it has been found that, in distilling the propylene oxide obtained from propylene and ethylbenzene hydroperoxide produced from ethylbenzene and molecular oxygen, the addition of a specific additive can suppress the side reaction to lower the loss of propylene oxide and enables efficient recovery of propylene oxide. Thus, the present invention has been accomplished.

According to the present invention, there is provided, in a process comprising the steps of oxidizing ethylbenzene in a liquid phase with molecular oxygen to obtain a reaction liquid containing ethylbenzene hydroperoxide, then distilling the reaction liquid to obtain a concentrated solution of ethylbenzene hydroperoxide, further mixing and reacting the concentrated solution with propylene to obtain a mixed solution containing propylene oxide, and distilling the mixed solution to separate and recover propylene oxide, the improvement in recovering propylene oxide wherein at least one compound selected from the group consisting of aliphatic saturated alcohols having 2–4 carbon atoms, allyl alcohol, saturated aliphatic hydrocarbons having 6 or 7 carbon atoms, benzene and compounds represented by the following chemical formulas (1)–(9) is added to the mixed solution in an amount of 0.01–100 parts by weight per 100 parts by weight of propylene oxide in the mixed solution.

 (1)

 (2)

 (3)

 (4)

 (5)

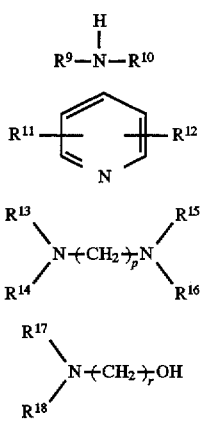

$$R^9-\overset{\underset{\mid}{H}}{N}-R^{10} \quad (6)$$

$$R^{11}-\underset{N}{\bigcirc}-R^{12} \quad (7)$$

$$\underset{R^{14}}{\overset{R^{13}}{\diagdown}}N\text{-}(CH_2\text{)}_p N\underset{R^{16}}{\overset{R^{15}}{\diagup}} \quad (8)$$

$$\underset{R^{18}}{\overset{R^{17}}{\diagdown}}N\text{-}(CH_2\text{)}_r OH \quad (9)$$

wherein the compounds represented by the formulas (1) and (2) have a boiling point at 1 atm of 60°–120° C.; the compounds represented by the formula (3) have a boiling point at 1 atm of 70°–120° C.; and $R^1$ to $R^{18}$, X, m, n, p and r in the formulas have the following meaning:

- in the formula (1), $R^1$ and $R^2$ are each independently an alkyl group having 1–4 carbon atoms,
- in the formula (2), X is a methylene group or an oxygen atom, and m and n are each independently an integer of 1 or 2,
- in the formula (3), $R^3$ is an alkyl group having 1–4 carbon atoms, $R^4$ is an alkyl group having 2–4 carbon atoms, provided that $R^3$ and $R^4$ may be linked with each other to form a ring,
- in the formula (4), $R^5$ is an alkyl group having 1–2 carbon atoms,
- in the formula (5), $R^6$, $R^7$ and $R^8$ are each independently an alkyl group having 1–10 carbon atoms, provided that any two of $R^6$, $R^7$ and $R^8$ may be linked with each other to form a ring structure,
- in the formula (6), $R^9$ and $R^{10}$ are each independently an isopropyl group or a t-butyl group,
- in the formula (7), $R^{11}$ and $R^{12}$ are each independently hydrogen or a methyl group,
- in the formula (8), $R^{13}$, $R^{14}$, $R^{15}$ and $R^{16}$ are each independently an alkyl group having 1–3 carbon atoms, and p is an integer of 2 or 3, and
- in the formula (9), $R^{17}$ and $R^{18}$ are each independently an alkyl group having 1–3 carbon atoms, and r is an integer of 2 or 3.

DETAILED DESCRIPTION OF THE INVENTION

In the present invention, the reaction liquid subjected to distillation is a mixed solution containing propylene oxide which is obtained by a process comprising the steps of oxidizing ethylbenzene in a liquid phase with molecular oxygen to obtain a reaction liquid containing ethylbenzene hydroperoxide, then distilling the reaction liquid to obtain a concentrated solution of ethylbenzene hydroperoxide, and mixing and reacting the concentrated solution with propylene to form propylene oxide. The above-mentioned process for obtaining the mixed solution is known to the art and is disclosed, for example, in U.S. Pat. No. 3,350,422 or U.S. Pat. No. 3,351,635.

The concentration of propylene oxide in the mixed solution is usually 3–30% by weight.

Components contained in the mixed solution other than propylene oxide are, for example, ethylbenzene, α-methylbenzyl alcohol, acetophenone, phenol, water, etc. The content of water is usually about 0.01–0.5% by weight, and the content of phenol is usually about 0.05–0.5% by weight. The mixed solution also contains trace amounts of carboxylic acids, such as formic acid, acetic acid and propionic acid. The contents of these acids are usually about 0.005–0.1% by weight.

In the present invention, an aliphatic saturated alcohol having 2–4 carbon atoms, allyl alcohol, a saturated aliphatic hydrocarbon having 6 or 7 carbon atoms, benzene, and a compound represented by the above-mentioned formulas (1)–(9) are used as an additive.

The aliphatic saturated alcohol having 2–4 carbon atoms may be, for example, ethyl alcohol, n-propyl alcohol, isopropyl alcohol, n-butyl alcohol, isobutyl alcohol, sec-butyl alcohol, and tert-butyl alcohol. Methyl alcohol, which has one carbon atom, is unpreferable because it has a boiling point near to that of propylene oxide and hence can be difficultly separated from propylene oxide. Aliphatic saturated alcohols having 5 or more carbon atoms are unpreferable because they sometimes increase the loss of propylene oxide.

The saturated aliphatic hydrocarbon having 6 or 7 carbon atoms may be, for example, n-hexane and n-heptane.

The compound represented by the formula (1) has a boiling point at 1 atm of 60°–120° C., and may be, for example, n-butyl methyl ether, n-propyl ether, n-propyl isopropyl ether and isopropyl ether.

The compound represented by the formula (2) has a boiling point at 1 atm of 60°–120° C. and may be, for example, tetrahydrofuran and 1,4-dioxane.

The compound represented by the formula (3) has a boiling point at 1 atm of 70°–120° C. and may be, for example, methyl ethyl ketone, methyl propyl ketone, 3-pentanone and methyl isobutyl ketone.

The compound represented by the formula (4) may be, for example, acetonitrile and propionitrile.

The compound represented by the formula (5) may be, for example, triethylamine, tripropylamine, tributylamine, diethylmethylamine, dimethylethylamine, dimethylisopropylamine, diisopropylethylamine, ethylpiperidine and methylpyrrolidine.

The compound represented by the formula (6) may be, for example, diisopropylamine and t-butylisopropylamine.

The compound represented by the formula (7) may be, for example, pyridine, lutidine, α-picoline, β-picoline and γ-picoline.

The compound represented by the formula (8) may be, for example, tetramethylethylenediamine, tetramethyltrimethylenediamine and tetraethylethylenediamine.

The compound represented by the formula (9) may be, for example, 2-dimethylaminoethanol, 3-dimethylaminopropanol and 2-diethylaminoethanol.

In the present invention, at least one compound selected from the group consisting of aliphatic saturated alcohols having 2–4 carbon atoms, allyl alcohol, saturated aliphatic hydrocarbons having 6 or 7 carbon atoms, benzene, and the compounds represented by the above formulas (1)–(9) is added to the solution to be distilled, and distillation is conducted in the presence of the added compound. The amount of the compound to be added relative to 100 parts by weight of propylene oxide is 0.01–100 parts by weight, preferably 0.05–100 parts by weight, more preferably 0.1–50 parts by weight, most preferably 0.1–10 parts by weight.

When the distillation is conducted with an addition of at least one compound selected from the group consisting of an aliphatic saturated alcohol having 2–4 carbon atoms, allyl alcohol, a saturated aliphatic hydrocarbon having 6 or 7 carbon atoms, benzene and compounds represented by one of the formulas (1)–(4), propylene oxide is distributed in the upper layer part in the distillation column and is recovered from the column top. Ethylbenzene, acetophenone, α-methylbenzyl alcohol and the like are distributed in the lower layer part in the distillation column and are recovered from the column bottom. Aliphatic saturated alcohols having 2–4 carbon atoms, allyl alcohol, saturated aliphatic hydrocarbons having 6 or 7 carbon atoms, benzene and compounds represented by the above formulas (1)–(4), which all have a boiling point in between the boiling point of propylene oxide and those of ethylbenzene, acetophenone and α-methylbenzyl alcohol, can be made to be so distributed as to have the concentration maximum in the middle layer part in the distillation column. In this instance, propylene oxide can be recovered from the column top and the organic acids and the like can be recovered from the column bottom; thus, the loss of propylene oxide can be suppressed. Also, water contained in the distillation feed material has a boiling point in between the boiling point of propylene oxide and those of ethylbenzene, acetophenone, α-methylbenzyl alcohol etc. and comes to be distributed to have the concentration maximum in the middle layer part in the distillation column. By proper control of the distillation conditions, the distribution of the water can be made to overlap the distribution of the aliphatic saturated alcohol having 2–4 carbon atoms, allyl alcohol, saturated aliphatic hydrocarbon having 6 or 7 carbon atoms, benzene, or compound represented by the above formulas (1)–(4) added as the additive. Consequently, the distillation can be conducted without a separation of a water layer in the distillation column, and the loss of propylene oxide can be suppressed. In the high water concentration region of the distillation column, also, the loss of propylene oxide can be suppressed through the dilution effect of the additive and the like.

Such effects of the additive can be attained by making the additive stationarily maintain the concentration maximum in the middle layer part of the distillation column. Accordingly, the distillation may be conducted either by feeding the additive at a constant rate or it may be conducted, after the amount of the additive staying in the column has become constant, by keeping the amount of the additive distilled out of the column at a very low level and feeding the additive in an amount matching therewith. The amount of the additive to be distilled out of the distillation column is preferably determined such that the amount of water in the distillation column may be kept at a proper level and no aqueous layer may be separated due to the retention of excessive amount of water in the column.

The additive may be fed to the distillation column either by adding it to the feed material in advance or by feeding it directly from an appropriate place of the column. When the additive needs to be recovered, it may be recovered either from the column top, or from the column bottom, or other appropriate place of the column. The recovered additive can be reused either as it is or after being purified.

When the compounds represented by the formulas (5)–(9) are used as the additive in the distillation, organic acids, molybdic acid, etc. in the distillation feed material are neutralized by the compounds represented by the formulas (5)–(9). Consequently, the side reactions of propylene oxide which might take place under acidic conditions can be suppressed and the loss of propylene oxide can be minimized.

When the compounds represented by the formulas (5)–(9) are fed as the additive, they may be added into the distillation feed material in advance, or they may be added to an appropriate place of the distillation column. When the recovery of the additive is necessary, it may be recovered either from the column top or from the column bottom or other appropriate place of the distillation column. The recovered additive can be reused either as it is or after being purified.

In the distillation according to the present invention, the temperature of the distillation column is preferably not lower than 135° C. When the difference of the column temperature from the column bottom temperature is small, the separation and recovery of propylene oxide is difficult.

The column top pressure in the distillation is preferably 0.5–5 atm, more preferably 1.0–3 atm, though it may vary depending on the kind of additives.

According to the present invention, propylene oxide can be efficiently separated and recovered, with suppressed side reactions and reduced loss of propylene oxide, from a reaction liquid containing propylene oxide which is obtained by a process comprising the steps of oxidizing ethylbenzene in a liquid phase with molecular oxygen to obtain a reaction liquid containing ethylbenzene hydroperoxide, then distilling the reaction liquid to obtain a concentrated solution of ethylbenzene hydroperoxide and further reacting the concentrated solution with propylene to form propylene oxide.

The present invention is described below in detail with reference to Examples. It is needless to say that the invention is in no way limited by the Examples.

EXAMPLES

Example 1

An initial charge liquid comprising 59.9% by weight of ethylbenzene, 30.2% by weight of α-methylbenzylalcohol, 5.6% by weight of acetophenone, 0.2% by weight of benzaldehyde and 0.2% by weight of phenol was charged into the bottom of a distillation column (number of stage: 34 as determined by a number of stage test using chlorobenzene and ethylbenzene; packing material: Helipack No. 2; column internal diameter: 30 mm) and heated in a nitrogen atmosphere at atmospheric pressure to initiate distillation.

The solution which was obtained from the epoxidation reaction of ethylbenzene hydroperoxide with propylene in the presence of a molybdenum based catalyst, had a composition of 10.37% by weight of propylene oxide, 50.73% by weight of ethylbenzene, 20.08% by weight of α-methylbenzyl alcohol and, as other trace components, 0.12% by weight of phenol, 0.063% by weight of water, 0.011% by weight of formic acid, 0.006% by weight of acetic acid, and 4.90% by weight (47.3% by weight relative to propylene oxide) of isopropyl alcohol which was added. The solution was fed at a rate of 200 g/hr from the stage at about the middle of the distillation column and distillation was continued. Thereafter, every two hours, distillates were withdrawn from the bottom, from the top and from the chimney part for separating and withdrawing water positioned at about the middle of the distillation column, then weighed and analyzed for their components. During the time, the temperature at the column top was 47°–60° C., the liquid temperature at the chimney part (the part for withdrawing water positioned at the 17th stage from the column bottom) was 69°–77° C., and the temperature of the column bottom was 147°–148° C. The distillation was carried out for 11 hours after the initiation of feeding the feed solution, during which a total of 2176.4 g of the solution was fed, and 303.1 g of a distillate from the column top and 1871.8 g of withdrawn liquid from the column bottom were obtained. Table 1 shows the operation conditions during 7 hours of the latter half of the distillation. No formation of a separated aqueous layer at the chimney part was observed.

The results of component analysis of the respective sampled liquids revealed that no propylene glycol had been formed which might be formed by the reaction of propylene oxide during distillation. Further, based on the results of analysis, material balance was calculated with the propylene glycol, the adduct of propylene glycol with propylene oxide, the adduct of phenol with propylene oxide, the adduct of α-methylbenzyl alcohol with propylene oxide, the adduct of formic acid and propylene oxide, the adduct of acetic acid with propylene oxide and the adduct of propionic acid with propylene oxide which had been formed by reaction during the distillation, and the rate of loss of propylene oxide during distillation relative to the fed propylene oxide was calculated. The result of the calculation revealed that no fed propylene oxide had been lost in the distillation and the fed propylene oxide had been recovered entirely.

Example 2

Distillation was carried out in the same manner as in Example 1 except that ethyl alcohol was used as the additive. The loss of PO determined in the same manner as in Example 1 from the results of analysis of samples collected in the latter half 9 hours of the distillation was 0.11%. Table 1 shows the operating conditions, etc. in the latter half 9 hours of the distillation.

Example 3

Distillation was carried out in the same manner as in Example 1 except that n-butyl alcohol was used as the additive. The loss of PO determined in the same manner as in Example 1 from the results of analysis of samples collected in the latter half 7 hours of the distillation was 0.32%. Table 1 shows the operating conditions, etc. in the latter half 7 hours of the distillation.

Example 4

Distillation was carried out in the same manner as in Example 1 except that n-propyl alcohol was used as the additive. The loss of PO determined in the same manner as in Example 1 from the results of analysis of samples collected in the latter half 7 hours of the distillation was 0.17%. Table 1 shows the operating conditions, etc. in the latter half 7 hours of the distillation.

Example 5

Distillation was carried out in the same manner as in Example 1 except that isobutyl alcohol was used as the additive and the feeding time of the distillation material was altered to 10 hours. The loss of PO determined in the same manner as in Example 1 from the results of analysis of samples collected in the latter half 6 hours of the distillation was 0.12%. Table 1 shows the operating conditions, etc. in the latter half 6 hours of the distillation.

Example 6

Distillation was carried out in the same manner as in Example 1 except that sec-butyl alcohol was used as the additive and the feeding time of the distillation material was altered to 10 hours. The loss of PO determined in the same manner as in Example 1 from the results of analysis of samples collected in the latter half 6 hours of the distillation was 0.23%. Table 2 shows the operating conditions, etc. in the latter half 6 hours of the distillation.

Example 7

Distillation was carried out in the same manner as in Example 1 except that tert-butyl alcohol was used as the additive and the feeding time of the distillation material was altered to 10 hours. The loss of PO determined in the same manner as in Example 1 from the results of analysis of samples collected in the latter half 6 hours of the distillation was nil. Table 2 shows the operating conditions, etc. in the latter half 6 hours of the distillation.

Example 8

Distillation was carried out in the same manner as in Example 1 except that allyl alcohol was used as the additive and the feeding time of the distillation material was altered to 10 hours. The loss of PO determined in the same manner as in Example 1 from the results of analysis of samples collected in the latter half 6 hours of the distillation was 0.18%. Table 2 shows the operating conditions, etc. in the latter half 6 hours of the distillation.

Example 9

Distillation was carried out in the same manner as in Example 1 except that the feeding time of the distillation material was altered to 102 hours. The loss of PO determined in the same manner as in Example 1 from the results of analysis of samples collected during the time from the 70th hour to the 102nd hour of distillation was 0.05%. The analysis of the samples also revealed that the isopropyl alcohol added in the distillation of this Example had been wholly recovered from the column top. Table 2 shows the operating conditions, etc. from the 70th hour to the 102nd hour of the distillation.

Example 10

Distillation was carried out in the same manner as in Example 1 except that the feeding time of the distillation materials was altered to 74 hours. The loss of PO determined in the same manner as in Example 1 from the results of analysis of samples collected during the time from the 52nd hour to the 74th hour of distillation was 0.66%. The analysis of the samples also revealed that the isopropyl alcohol added in the distillation of this Example had been nearly wholly recovered from the column bottom. Table 2 shows the operating conditions, etc. from the 52nd hour to the 74th hour of the distillation.

Example 11

Distillation was carried out in the same manner as in Example 1 except that n-propyl alcohol was used as the additive and the feeding time of the distillation material was altered to 77 hours. The loss of PO determined in the same manner as in Example 1 from the results of analysis of samples collected during the time from the 52nd hour to the 77th hour of distillation was 0.04%. The analysis of the samples also revealed that the n-propyl alcohol added in the distillation of this Example had been wholly recovered from the column bottom. Table 3 shows the operating conditions, etc. from the 52nd hour to the 77th hour of the distillation.

Example 12

Distillation was carried out in the same manner as in Example 1 except that n-propyl alcohol was used as the additive, the feeding time of the distillation material was altered to 96 hours, and the amount of n-propyl alcohol added was 2% by weight until the 24th hour of distillation, 0.2% by weight from the 24th hour to the 32nd hour of distillation, and 0.03% by weight from the 32nd hour to the 96th hour of distillation. The loss of PO determined in the same manner as in Example 1 from the results of analysis of samples collected during the time from the 58th hour to the 96th hour of distillation was 0.06%. The recovery of PO was 99.8%. Table 3 shows the operating conditions, etc. from the 58th hour to the 96th hour of the distillation.

Comparative Examples 1 and 2

Distillation was carried out in the same manner as in Example 1 except that no additive was added and the distillation time was altered to 8 hours per day for 2 days. The loss of PO determined in the same manner as in Example 1 from the results of analysis of samples was 1.17% (Comparative Example 1) or 1.06% (Comparative Example 2). Table 3 shows the operating conditions, etc.

Comparative Example 3

Distillation was carried out in the same manner as in Example 1 except that methanol was added as the additive. The loss of PO determined in the same manner as in Example 1 from the results of analysis of samples was 1.02%. Table 3 shows the operating conditions, etc.

TABLE 1

|  | Example | | | | |
| --- | --- | --- | --- | --- | --- |
|  | 1 | 2 | 3 | 4 | 5 |
| Alcohol *1) | | | | | |
| Kind | iPrOH | EtOH | BUOH | nPrOH | iBuOH |
| Amount (wt. %) | 5 | 5 | 4 | 5 | 5 |
| Distillation conditions | | | | | |
| Temperature (°C.) | | | | | |
| Top | 55–57 | 46–54 | 30 | 56–63 | 31 |
| Bottom | 147–148 | 148 | 162–163 | 142–148 | 138–139 |
| Top pressure (kg/cm$^2$) | Atmospheric | Atmospheric | Atmospheric | Atmospheric | Atmospheric |
| Reflux ratio *2) | 3/1 | 3/1 | 3/1 | 3/1 | 3/2 |
| Feed liquid (g) | 1390.3 | 1816.1 | 1418.0 | 1401.0 | 1198.2 |
| Recovered liquid (g) | | | | | |
| Top | 211.2 | 258.4 | 131.1 | 178.6 | 117.7 |
| Chimney separated water | 0 | 0.1 | 0.2 | 0 | 0 |
| Bottom | 1148.4 | 1529.0 | 1246.8 | 1180.5 | 1043.6 |
| Results *3) | | | | | |
| Residual PO (wt. %) | 0 | 0 | 0 | 0 | 0 |
| PO loss (%) | 0 | 0.11 | 0.32 | 0.17 | 0.12 |
| PG formed (%) | 0 | 0 | 0.03 | 0.09 | 0.08 |

TABLE 2

| | Example | | | | |
|---|---|---|---|---|---|
| | 6 | 7 | 8 | 9 | 10 |
| **Alcohol *1)** | | | | | |
| Kind | secBuOH | tBuOH | AlOH | iPrOH | iPrOH |
| Amount (wt. %) | 5 | 5 | 5 | 3 | 2 |
| Distillation conditions | | | | | |
| Temperature (°C.) | | | | | |
| Top | 41–44 | 56–60 | 57–64 | 45–54 | 31–41 |
| Bottom | 139–146 | 146–148 | 146–148 | 147–148 | 137–151 |
| Top pressure (kg/cm$^2$) | Atmospheric | Atmospheric | Atmospheric | Atmospheric | Atmospheric |
| Reflux ratio *2) | 3/2 | 3/2 | 3/2 | 3/2 | 3/2 |
| Feed liquid (g) | 1198.9 | 1200.2 | 1403.2 | 20508.8 | 14385.9 |
| Recovered liquid (g) | | | | | |
| Top | 139.5 | 181.1 | 177.9 | 2812.8 | 1464.7 |
| Chimney separated water | 0 | 0 | 0 | 0.3 | 0 |
| Bottom | 1025.4 | 997.2 | 1193.3 | 17386.6 | 12703.6 |
| **Results *3)** | | | | | |
| Residual PO (wt. %) | 0 | 0 | 0 | 0 | 0 |
| PO loss (%) | 0.23 | 0 | 0.18 | 0.05 | 0.66 |
| PG formed (%) | 0.15 | 0 | 0.11 | 0 | 0.59 |

TABLE 3

| | Example | | Comparative Example | | |
|---|---|---|---|---|---|
| | 11 | 12 | 1 | 2 | 3 |
| **Alcohol *1)** | | | | | |
| Kind | nPrOH | nPrOH | — | — | MeOH |
| Amount (wt. %) | 2 | 4 | 0 | 0 | 5 |
| Distillation conditions | | | | | |
| Temperature (°C.) | | | | | |
| Top | 27–34 | 33–34 | 30–31 | 29–31 | 38–42 |
| Bottom | 140–153 | 150–151 | 148–150 | 147–148 | 148 |
| Top pressure (kg/cm$^2$) | Atmospheric | Atmospheric | Atmospheric | Atmospheric | Atmospheric |
| Reflux ratio *2) | 3/2 | 3/2 | 3/1 | 3/1 | 3/1 |
| Feed liquid (g) | 15453.5 | 19318.9 | 3247.0 | 3215.1 | 1801.0 |
| Recovered liquid (g) | | | | | |
| Top | 1512.9 | 2167.4 | 326.1 | 323.8 | 240.2 |
| Chimney separated water | 0 | 0 | 14.3 | 11.7 | 0.4 |
| Bottom | 13509.6 | 16835.6 | 2876.4 | 2860.0 | 1513.5 |
| **Results *3)** | | | | | |
| Residual PO (wt. %) | 0 | 0 | 0 | 0 | 0 |
| PO loss (%) | 0.04 | 0.06 | 1.17 | 1.06 | 1.02 |
| PG formed (%) | 0 | 0 | 0.60 | 0.49 | 0.57 |

Note
*1) Alcohol
Kind
iPrOH: isopropyl alcohol
EtOH: ethyl alcohol
nBuOH: n-butyl alcohol
nPrOH: n-propyl alcohol
iBuOH: isobutyl alcohol
secBuOH: sec-butyl alcohol
tBuOH: tert-butyl alcohol
AlOH: allyl alcohol
Added Amount:parts by weight per 100 parts by weight of mixture subjected to distillation
*2) Reflux ratio = amount refluxed from top/total amount distilled out
*3) Result
Residual PO: % by weight of propylene oxide remaining in bottom liquid
PO loss = $(K_2 - K_1) \times 100$/number of mole of propylene oxide in feed solution, wherein TABLE 3-continued

|  | Example | | Comparative Example | | |
|---|---|---|---|---|---|
|  | 11 | 12 | 1 | 2 | 3 |

$K_1$: total number of mole of propylene glycol, adduct of propylene glycol with propylene oxide, adduct of phenol with propylene oxide, adduct of α-methylbenzyl alcohol with propylene oxide, adduct of formic acid with propylene oxide, adduct of acetic acid with propylene oxide and adduct of propionic acid with propylene oxide in feed solution.
$K_2$: total number of mole of propylene glycol, adduct of propylene glycol with propylene oxide, adduct of phenol with propylene oxide, adduct of α-methylbenzyl alcohol with propylene oxide, adduct of formic acid with propylene oxide, adduct of acetic acid with propylene oxide and adduct of propionic acid with propylene oxide in distillates (distillate from top, water distilled out from chimney part and distillate from bottom)
PG formed = $(PG_2 - PG_1) \times 100$/number of mole of propylene oxide in feed solution, wherein
$PG_1$: number of mole of propylene glycol in feed solution
$PG_2$: number of mole of propylene glycol in distillates (distillate from top, water distilled out from chimney part and distillate from bottom)
*4) 2% by weight till the 24th hour of distillation, 0.2% by weight from the 24th till the 32nd hour of distillation, 0.03% by weight on and after the 32nd hour of distillation

Example 13

An initial charge liquid comprising 11.2 g of propylene oxide, 152.1 g of ethylbenzene, 67.7 g of α-methylbenzyl alcohol, 11.1 g of acetophenone, 0.4 g of benzaldehyde, 0.4 g of phenol and 0.1 g of propylene glycol was charged into the bottom of a distillation column (number of stage: 34 as determined by a number of stage test using chlorobenzene and ethylbenzene; packing material: Helipack No. 2; column internal diameter: 30 mm) and heated in a nitrogen atmosphere at atmospheric pressure to initiate distillation.

The solution which was obtained from the epoxidation reaction of ethylbenzene hydroperoxide with propylene in the presence of a molybdenum based catalyst, had a composition of 10.85% by weight of propylene oxide, 52.45% by weight of ethylbenzene, 26.19% by weight of α-methylbenzyl alcohol and, as other trace components, 0.16% by weight of phenol, 0.091% by weight of water, 0.011% by weight of formic acid, 0.005% by weight of acetic acid and 1.03% by weight (9.5% by weight relative to propylene oxide) of tetrahydrofuran which was added. The solution was fed at a rate of 200 g/hr from the stage at about the middle of the distillation column, and distillation was continued. Thereafter, every two hours, distillates were withdrawn from the bottom, from the top and from the chimney part for separating and withdrawing water positioned at about the middle of the distillation column, then weighed and analyzed for their components.

During the time, the distillation was run at a column top temperature of 30° C., a liquid temperature of the chimney part of 76°–80° C. and a column bottom temperature of 148°–150° C. The distillation was conducted for 8 hours from the initiation of feeding the feed solution. During the distillation, 1626.0 g of the solution was fed, and 172.2 g of distillate from the column top, 1.5 g of aqueous solution from the chimney part and 1353.9 g of distillate from the column bottom were obtained. Thus, the distillation of the first day was finished.

On the second day, the bottom liquid held in the bottom when the distillation of the proceeding day was discontinued was boiled up and, from about 1 hour thereafter, distillation was carried out by feeding 1593.3 g of the same solution as used in the proceeding day in the course of 8 hours, to keep about the same rate of 200 g/hr as in the proceeding day. Every two hours, distillates were withdrawn from the bottom, top and chimney part, then weighed and analyzed for their components. The distillation was operated at a column top temperature of 30°–33° C., chimney part liquid temperature of 76°–80° C. and a column bottom temperature of 148° C., and finished after 8 hours from the initiation of feeding the solution. In this distillation 150.2 g of distillate was obtained from the top, 1.6 g of aqueous solution from the chimney part, and 1360.4 g of distillate from the bottom.

After finishing the aforesaid distillation, 23.1 g of organic matter and 0.2 g of aqueous solution were obtained from the chimney part and 285.4 g of organic matter was obtained from the column bottom.

From the results of component analysis of the same liquids collected during distillation, increase or decrease in the amount of was calculated with propylene glycol, the adduct of propylene glycol with propylene oxide, the adduct of phenol with propylene oxide, the adduct of α-methylbenzyl alcohol with propylene oxide, the adduct of formic acid with propylene oxide, the adduct of acetic acid with propylene oxide and the adduct of propionic acid with propylene oxide which had been formed by the reaction of propylene oxide during distillation. The distillation loss of propylene oxide expressed in terms of % by mole relative to fed propylene oxide was found to be 0.44% by mole per hour. Table 4 shows the conditions and the results of the distillation.

Example 14

Distillation was carried out in the same manner as in Example 13 except that a feed solution containing 1% by weight of diisopropyl ether added as the additive was used. The distillation loss of propylene oxide relative to fed propylene oxide determined from the analysis of samples collected during the latter half 6 hours of the second day of distillation was zero % by mole. Table 4 shows the distillation conditions, etc. in the latter half 6 hours of the second day of distillation.

Example 15

Distillation was carried out in the same manner as in Example 13 except that a feed solution containing 1% by weight of n-propyl ether added as the additive was used and further 50 g of n-propyl ether of the additive was additionally charged into the column bottom in advance. Table 4 shows the distillation conditions, etc.

Example 16

Distillation was carried out in the same manner as in Example 13 except that a feed solution containing 5% by weight of methyl ethyl ketone added as the additive was used. Table 4 shows the distillation conditions, etc.

Example 17

Distillation was carried out in the same manner as in Example 13 except that a feed solution containing 5% by weight of methyl isobutyl ketone added as the additive was used and that distillation was conducted for only one day. The distillation loss of propylene oxide determined in the same manner as described above from the analysis of samples collected during the latter half 10 hours of the distillation was 0.51% by mole. Table 4 shows the distillation conditions, etc. in the latter half 10 hours of the distillation.

Example 18

Distillation was carried out in the same manner as in Example 13 except that a feed solution containing 5% by weight of methyl n-propyl ketone added as the additive was used and that distillation was conducted for only one day with the liquid feeding time altered to 11 hours. The distillates were withdrawn for analysis every two hours till the 10th hour from the initiation of feeding the solution, but the final samples were withdrawn at the end of the last one hour. The distillation loss of propylene oxide determined in the same manner as above from the analysis of samples collected during the latter half 7 hours of the distillation was 0.18% by mole. Table 5 shows the distillation conditions, etc. in the latter half 7 hours of the distillation.

Example 19

Distillation was carried out in the same manner as in Example 18 except that a feed solution containing 5% by weight of 3-methyl-2-butanone added as the additive was used. The distillation loss of propylene oxide determined in the same manner as described above was 0.32% by mole. Table 5 shows the distillation conditions, etc.

Comparative Example 4

Distillation was carried out in the same manner as in Example 18 except that a feed solution containing 5% by weight of acetone added as the additive was used. The recovery of propylene oxide was 96.5% and the loss of propylene oxide was 3.5%. Table 5 shows the distillation conditions, etc.

Example 20

Distillation was carried out in the same manner as in Example 18 except that a feed solution containing 5% by weight of benzene added as the additive was used. The distillation loss of propylene oxide determined in the same manner as described above from the analysis of samples collected in the latter half 9 hours of the distillation was zero % by mole. Table 5 shows the distillation conditions, etc. in the latter half 9 hours of the distillation.

Example 21

Distillation was carried out in the same manner as in Example 20 except that a feed solution containing 5% by weight of n-hexane added as the additive was used. The distillation loss of propylene oxide determined in the same manner as described above was 0.12% by mole. Table 5 shows the distillation conditions, etc.

Example 22

Distillation was carried out in the same manner as in Example 20 except that a feed solution containing 5% by weight of n-heptane added as the additive was used. The distillation loss of propylene oxide determined in the same manner as above was zero by mole. Table 5 shows the distillation conditions, etc.

Example 23

Distillation was carried out in the same manner as in Example 20 except that a feed solution containing 5% by weight of acetonitrile added as the additive was used. The distillation loss of propylene oxide determined in the same manner as above was 0.04% by mole. Table 6 shows the distillation conditions, etc.

Example 24

Distillation was carried out in the same manner as in Example 20 except that a feed solution containing 5% by weight of dioxane added as the additive was used. The distillation loss of propylene oxide determined in the same manner as above was 0.32% by mole. Table 6 shows the distillation conditions, etc.

Example 25

Distillation was carried out in the same manner as in Example 13 except that a feed solution containing 1% by weight of tetrahydrofuran added as the additive was used and the feeding time of the distillation material was altered to 24 hours. The distillation loss of propylene oxide determined from the analysis of samples collected at the 22nd and 24th hour of the distillation was 0.29% by mole. Table 6 shows the results of distillation from the initiation of feeding the distillation liquid till the sampling at the 24th hour.

TABLE 4

|  | Example | | | | |
| --- | --- | --- | --- | --- | --- |
|  | 13 | 14 | 15 | 16 | 17 |
| Added compound *1) | | | | | |
| Kind | THF | (1)-1 | (1)-2 | MEK | MIBK |
| Amount (wt. %) | 1 | 1 | 1 | 5 | 5 |
| Distillation conditions | | | | | |
| Temperature (°C.) | | | | | |
| Top | 30–33 | 30–35 | 30–31 | 47–51 | 30 |
| Bottom | 148–150 | 148 | 148 | 148 | 145–146 |
| Top pressure (kg/cm$^2$) *2) | ata | ata | ata | ata | ata |

TABLE 4-continued

|  | Example | | | | |
|---|---|---|---|---|---|
|  | 13 | 14 | 15 | 16 | 17 |
| Reflux ratio *3) | 3/1 | 3/1 | 3/1 | 3/1 | 3/1 |
| Feed liquid (g) | 3219.3 | 1190.9 | 1195.2 | 1195.8 | 2014.4 |
| Recovered liquid (g) | | | | | |
| Top | 322.4 | 138.5 | 124.3 | 185.9 | 186.5 |
| Chimney separated water | 3.1 | 0.3 | 0.3 | 0 | 1.5 |
| Bottom | 2714.3 | 1021.7 | 1046.3 | 978.5 | 1771.2 |
| Results *4) | | | | | |
| Residual PO (wt. %) | 0 | 0 | 0 | 0 | 0 |
| PO loss (%) | 0.44 | 0 | 0 | 0 | 0.51 |

TABLE 5

|  | Example | | | | | Comparative Example |
|---|---|---|---|---|---|---|
|  | 18 | 19 | 20 | 21 | 22 | 4 |
| Added compound *1) | | | | | | |
| Kind | (3)-1 | (3)-2 | Benzene | n-Hexane | n-Hexane | Acetone |
| Amount (wt. %) | 5 | 5 | 5 | 5 | 5 | 5 |
| Distillation conditions | | | | | | |
| Temperature (°C.) | | | | | | |
| Top | 41–58 | 55–70 | 52–54 | 36–40 | 67–70 | 38 |
| Bottom | 144 | 148 | 148 | 148 | 148 | 148 |
| Top pressure *2) | ata | ata | ata | ata | ata | ata |
| Reflux ratio *3) | 3/1 | 3/1 | 3/1 | 3/1 | 3/1 | 3/1 |
| Feed liquid (g) | 1384.4 | 1383.1 | 1781.7 | 1798.9 | 1818.7 | 2008.7 |
| Recovered liquid (g) | | | | | | |
| Top | 145.9 | 188.9 | 245.6 | 276.1 | 252.7 | 296.2 |
| Chimney separated water | 0 | 0 | 0.4 | 2.7 | 0.2 | 4.8 |
| Bottom | 1206.7 | 1160.3 | 1500.4 | 1487.6 | 1522.6 | 1673.6 |
| Results *4) | | | | | | |
| Residual PO (wt. %) | 0 | 0 | 0 | 0 | 0 | 0 |
| PO loss (%) | 0.18 | 0.32 | 0 | 0.12 | 0 | 3.5*5) |

TABLE 6

|  | Example | | |
|---|---|---|---|
|  | 23 | 24 | 25 |
| Added compound *1) | | | |
| Kind | AN | Dioxane | THF |
| Amount (wt. %) | 5 | 5 | 1 |
| Distillation conditions | | | |
| Temperature (°C.) | | | |
| Top | 45–56 | 31–38 | 30–32 |
| Bottom | 148 | 145–148 | 148–150 |
| Top pressure *2) | ata | ata | ata |
| Reflux ratio *3) | 3/1 | 3/1 | 3/1 |
| Feed liquid (g) | 1803.2 | 1800.1 | 4930.0 |
| Recovered liquid (g) | | | |
| Top | 265.6 | 182.8 | 553.5 |
| Chimney separated water | 0 | 0 | 0 |
| Bottom | 1511.0 | 1558.4 | 4151.1 |
| Results *4) | | | |
| Residual PO (wt. %) | 0 | 0 | 0 |
| PO loss (%) | 0.04 | 0.32 | 0.29 |

Note:
*1) Added compound
Kind
(1)-1: diisopropyl ether
(1)-2: n-propyl ether
MEK: methyl ethyl ketone
MIBK: methyl isobutyl ketone
(3)-1: methyl n-propyl ketone
(3)-2: 3-methyl-2-butanone
AN: acetonitrile
Amount: parts by weight per 100 parts by weight of mixture subjected to distillation
*2) Top pressure TABLE 6-continued

| | Example | | |
|---|---|---|---|
| | 23 | 24 | 25 | ata: atmosphere absolute (atmospheric pressure)
*3) Reflux ratio = amount refluxed from top/total amount distilled out
*4) Result
Residual PO: % by weight of propylene oxide remaining in bottom liquid
PO loss = $(K_2 - K_1) \times 100$/number of moles of propylene oxide in feed solution, wherein
$K_1$: total number of mole of propylene glycol, adduct of propylene glycol with propylene oxide, adduct of phenol with propylene oxide, adduct of α-methylbenzyl alcohol with propylene oxide, adduct of formic acid with propylene oxide, adduct of acetic acid with propylene oxide and adduct of propionic acid with propylene oxide in feed solution,
$K_2$: total number of mole of propylene glycol, adduct of propylene glycol with propylene oxide, adduct of phenol with propylene oxide, adduct of α-methylbenzyl alcohol with propylene oxide, adduct of formic acid with propylene oxide, adduct of acetic acid with propylene oxide and adduct of propionic acid with propylene oxide in distillates (distillate from top, water distilled out from chimney part and distillate from bottom)
*5)value obtained by subtracting the recovery (in %) of propylene oxide from 100%.

Example 26

An initial charge liquid comprising 9.1 g of propylene oxide, 136.9 g of ethylbenzene, 48.8 g of α-methylbenzyl alcohol, 6.9 g of acetophenone, 0.3 g of benzaldehyde, 0.3 g of phenol and 0.4 g of propylene glycol was charged into the bottom of a distillation column (number of stage: 34 as determined by a number of stage test using chlorobenzene and ethylbenzene; packing material: Helipack No. 2; column internal diameter: 30 mm) and heated in a nitrogen atmosphere at atmospheric pressure to initiate distillation.

The solution which was obtained from the epoxidation reaction of ethylbenzene hydroperoxide with propylene in the presence of a molybdenum based catalyst, had a composition of 10.9% by weight of propylene oxide, 55.3% by weight of ethylbenzene, 25.4% of α-methylbenzyl alcohol and, as other trace components, 0.15% by weight of phenol, 0.095% by weight of water, 0.010% by weight of formic acid, 0.005% by weight of acetic acid and 0.027% by weight (0.25% by weight relative to propylene oxide) of triethylamine which was added. The solution was fed at a rate of 200 g/hr from the stage at about the middle of the distillation column, and distillation was continued. Thereafter, every two hours, distillates were withdrawn from the bottom, from the top, and from the chimney part for separating and withdrawing water positioned at about the middle of the distillation column, then weighed and analyzed for their components.

During the time, the distillation was run at a column top temperature of 30°–31° C., a liquid temperature of the chimney part of 76°–80° C., and a column bottom temperature of 146°–148° C. The distillation was conducted for 8 hours from the initiation of feeding the feed solution. During the distillation, 1624.0 g of the solution was fed, and 165.0 g of distillate from the column top, 3.2 g of aqueous solution from the chimney part and 1576.0 g of distillate from the column bottom were obtained. Thus, the distillation of the first day was finished.

On the second day, the bottom liquid held in the bottom when distillation was discontinued on the preceding day was boiled up and, from about 1 hour thereafter, distillation was carried out by feeding 1603.6 g of the same solution as used in the preceding day in the course of 8 hours to keep about the same rate of 200 g/hr as in the preceding day. Every two hours, distillates were withdrawn from the bottom, top and chimney part, then weighed and analyzed for their components. The distillation was operated at a column top temperature of 30°–30.5° C., chimney part liquid temperature of 79°–82° C. and column bottom temperature of 146° C., and was finished after 8 hours from the initiation of feeding the solution. In this distillation 170.41 g of distillate was obtained from the top, 5.4 g of aqueous solution from the chimney part, and 1539.7 g of distillate from the bottom.

After finishing the aforesaid distillation, 21.7 g of organic matter and 0.7 g of aqueous solution were obtained from the chimney part and 228.2 g of organic matter was obtained from the column bottom.

From the results of component analysis of the sample liquids collected during distillation, increase or decrease in the amount was calculated with propylene glycol, the adduct of propylene glycol with propylene oxide, the adduct of phenol with propylene oxide, the adduct of α-methylbenzyl alcohol with propylene oxide, the adduct of formic acid with propylene oxide, the adduct of acetic acid with propylene oxide and the adduct of propionic acid with propylene oxide which had been formed by the reaction of propylene oxide during distillation. The distillation loss of propylene oxide expressed in terms of % by mole relative to fed propylene oxide was found to be 0.34% by mole per hour.

Example 27

An initial charge liquid comprising 11.3 g of propylene oxide, 155.5 g of ethylbenzene, 68.4 g of α-methylbenzyl alcohol, 9.9 g of acetophenone, 0.36 g of benzaldehyde, 0.40 g of phenol and 0.66 g of propylene glycol was charged into the bottom of a distillation column (number of stage: 34 as determined by a number of stage test using chlorobenzene and ethylbenzene; packing material: Helipack No. 2; column internal diameter: 30 mm) and heated in a nitrogen atmosphere at atmospheric pressure to initiate distillation.

The solution which was obtained from the epoxidation reaction of ethylbenzene hydroperoxide with propylene in the presence of a molybdenum based catalyst, had a composition of 10.9% by weight of propylene oxide, 52.6% by weight of ethylbenzene, 27.7% by weight of α-methylbenzyl alcohol and, as other trace components, 0.16% by weight of phenol, 0.073% by weight of water, 0.012% by weight of formic acid and 0.006% by weight of acetic acid. Distillation was carried out by feeding the aforesaid solution at a rate of 200 g/hr from the stage at about the middle of the distillation column and simultaneously feeding a 5% by weight ethylbenzene solution of triethylamine at a rate of about 18.9 g/hr from the upper part of the distillation material feeding stage. Thereafter, every two hours, distillates were withdrawn from the bottom, from the top and from the chimney part for separating and withdrawing water positioned at about the middle of the distillation column, then weighed and analyzed for their components.

During the time, the distillation was run at a column top temperature of 30°–31° C., a liquid temperature of the chimney part of 78°–80° C., and a column bottom temperature of 146°–148° C. The distillation was conducted for 8 hours from the initiation of feeding the feed solution, and 1624.0 g of the solution was fed. The 5% by weight ethylbenzene solution of triethylamine was fed in a total amount of 153.8 g in the course of 8 hours from the initiation of feeding.

As the result of this distillation, 165.0 g of distillate from the column top, 3.2 g of aqueous solution from the chimney part and 1571.0 g of distillate from the column bottom were obtained. Thus, the distillation of the first day was finished.

On the second day, the bottom liquid held in the bottom when distillation was discontinued on the preceding day was boiled up and, from about one hour thereafter, distillation was carried out by feeding 1603.6 g of the same distillation material solution as used in the preceding day in the course of 8 hours to keep about the same rate of 200 g/hr as in the preceding day, and concurrently feeding 154.7 g of 5% by weight ethylbenzene solution of triethylamine at a rate of about 18.9 g/hr. Every two hours, distillates were withdrawn from the bottom, top and chimney part, then weighed and analyzed for their components. The distillation was operated at a column top temperature of 30°–30.5° C., a chimney part liquid temperature of 77°–80° C. and a column bottom temperature of 146°–147° C., and was finished after 8 hours from the initiation of feeding the solution. In the distillation, 170.5 g of distillate was obtained from the top, 5.4 g of aqueous solution from the chimney part, and 1539.7 g of distillate from the bottom.

After finishing the aforesaid distillation, 21.7 g of organic matter and 0.7 of aqueous solution were obtained from the chimney part and 228.2 g of organic matter was obtained from the column bottom.

From the results of component analysis of the sample liquids collected during distillation, increase or decrease in the amount was calculated with propylene glycol, the adduct of propylene glycol with propylene oxide, the adduct of phenol with propylene oxide, the adduct of α-methylbenzyl alcohol with propylene oxide, the adduct of formic acid with propylene oxide, the adduct of acetic acid with propylene oxide and the adduct of propionic acid with propylene oxide which had been formed by the reaction of propylene oxide during distillation. The distillation loss of propylene oxide expressed in terms of % by mole relative to fed propylene oxide was found to be 0.27% by mole per hour.

The loss of propylene oxide caused in the distillation and separation of propylene oxide can mostly be attributed to the hydration of propylene oxide to form propylene glycol and the further reaction of propylene glycol with propylene oxide to form oligomers or polymers.

The hydration of propylene oxide is further accelerated under acidic conditions.

The effect of addition of organic amines in preventing the loss of propylene oxide which might occur by conversion of propylene oxide into propylene glycol and other by-products through hydration under acidic conditions, wherein organic acids, etc. are present, was confirmed in the following manner.

Example 28

A mixture of 136.6 g of water, 0.63 g of acetic acid, 12.0 g of propylene oxide and 1.36 g of diisopropylethylamine as an organic amine additive was stirred at 43° C. for 7 hours.

Analysis after the reaction showed that 7.38% by mole of propylene glycol and 0.04% by mole of dipropylene glycol had been formed relative to charged propylene oxide. No formation of tripropylene glycol was observed. The total loss of propylene oxide was 7.42% by mole relative to charged propylene oxide.

Examples 29–43 and Comparative Example 5

The same procedures as in Example 28 were repeated to examine the loss of propylene oxide except for changing the added organic amines. The results obtained are shown in Tables 7–10.

TABLE 7

|  | Comparative Example 5 | Example 29 | Example 30 | Example 31 |
|---|---|---|---|---|
| Added compound |  |  |  |  |
| Kind *1) | (Acidic *4) | (5)-1 | (5)-2 | (5)-3 |
| Amount *2) |  | 1.0 | 1.0 | 1.0 |
| Result PO loss (%) *3) |  |  |  |  |
| PG | 95.40 | 10.10 | 10.46 | 9.13 |
| POPG | 1.82 | 0.05 | 0.09 | 0.08 |
| TPG | 0.02 | — | — | — |
| PO ACD | 0.11 | 0.11 | 0.04 | 0.26 |
| Total | 97.35 | 10.26 | 10.59 | 9.47 |

TABLE 8

|  | Example 32 | Example 33 | Example 34 | Example 35 | Example 36 |
|---|---|---|---|---|---|
| Added compound |  |  |  |  |  |
| Kind *1) | (5)-4 | (5)-5 | (5)-6 | (5)-7 | (6)-1 |
| Amount *2) | 1.0 | 1.0 | 1.0 | 1.0 | 1.0 |
| Result PO loss (%) *3) |  |  |  |  |  |
| PG | 9.68 | 10.95 | 9.73 | 7.38 | 7.40 |
| POPG | 0.08 | 0.09 | 0.13 | 0.04 | 0.04 |
| TPG | — | — | — | — | — |
| PO ACD | 0.19 | 0.09 | 0.09 | 0.56 | 0.56 |
| Total | 9.95 | 11.13 | 9.95 | 7.98 | 8.00 |

TABLE 9

|  | Example 37 | Example 38 | Example 39 | Example 40 |
|---|---|---|---|---|
| Added compound |  |  |  |  |
| Kind *1) | (6)-2 | (7)-1 | (7)-2 | (7)-3 |
| Amount *2) | 1.0 | 1.0 | 1.0 | 1.0 |
| Result PO loss (%) *3) |  |  |  |  |
| PG | 8.04 | 10.12 | 7.00 | 9.35 |
| POPG | 0.06 | 0.08 | 0.05 | 0.09 |
| TPG | — | — | — | — |
| PO ACD | 0.53 | 0.04 | 0.93 | 0.91 |
| Total | 8.63 | 10.24 | 7.98 | 10.35 |

TABLE 10

|  | Example 41 | Example 42 | Example 43 |
|---|---|---|---|
| Added compound |  |  |  |
| Kind *1) | (5)-8 | (8)-1 | (9)-1 |
| Amount *2) | 1.0 | 1.0 | 1.0 |
| Result PO loss (%) *3) |  |  |  |
| PG | 10.21 | 23.55 | 10.15 |
| POPG | 0.06 | 1.06 | 0.07 |

TABLE 10-continued

|     | Example 41 | Example 42 | Example 43 |
|-----|------------|------------|------------|
| TPG | —          | —          | —          |
| PO ACD | 0.12    | 0.04       | 0.11       |
| Total | 10.39    | 24.65      | 10.33      |

Note:
*1) Kind of added compound
(5)-1: triethylamine
(5)-2: ethylpiperidine
(5)-3: methylpyrrolidine
(5)-4: diethylmethylamine
(5)-5: dimethylethylamine
(5)-6: dimethylisopropylamine
(5)-7: diisopropylethylamine
(6)-1: diisopropylamine
(6)-2: t-butylisopropylamine
(7)-1: pyridine
(7)-2: lutidine
(7)-3: α-picoline
(5)-8: tri-n-butylamine
(8)-1: tetramethylethylenediamine
(9)-1: 2-dimethylaminoethanol
*2) Amount of added compound: molar ratio of the compound to acid
*3) Po loss: propylene oxide loss
PG: propylene glycol
POPG: dipropylene glycol
TPG: tripropylene glycol
PO ACD: adduct of propylene oxide with acetic acid
*4) (acidic): Reaction was carried out under the same conditions as in Example 28 except that no organic amine was added.

What is claimed is:

1. A process comprising the steps of oxidizing ethylbenzene in a liquid phase with molecular oxygen to obtain a reaction liquid containing ethylbenzene hydroperoxide, then distilling the reaction liquid to obtain a concentrated solution of ethylbenzene hydroperoxide, further mixing and reacting the concentrated solution with propylene to obtain a mixed solution containing propylene oxide, ethylbenzene, acetophenone, and α-methylbenzyl alcohol, then distilling the mixed solution to separate propylene oxide from the ethylbenzene, acetophenone, and α-methylbenzyl alcohol and recover propylene oxide, wherein at least one compound selected from the group consisting of aliphatic saturated alcohols having 2–4 carbon atoms, allyl alcohol, and compounds represented by the following chemical formulas (1)–(4) is added to the mixed solution in an amount of 0.05–100 parts by weight per 100 parts by weight of propylene oxide in the mixed solution:

$$R^1-O-R^2 \quad (1)$$

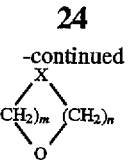  (2)

$$\underset{R^3-C-R^4}{\overset{O}{\|}} \quad (3)$$

$$R^5-CN \quad (4)$$

wherein the compounds represented by the formulas (1) and (2) have a boiling point at 1 atm of 60°–120° C.; the compounds represented by the formula (3) have a boiling point at 1 atm of 70°–120° C.; and $R^1$ to $R^5$, X, m, and n in the formulas have the following meaning:

in the formula (1), $R^1$ and $R^2$ are each independently an alkyl group having 1–4 carbon atoms, in the formula (2), X is a methylene group or an oxygen atom, and m and n are each independently an integer of 1 or 2, in the formula (3), $R^3$ is an alkyl group having 1–4 carbon atoms, $R^4$ is an alkyl group having 2–4 carbon atoms, provided that $R^3$ and $R^4$ may be linked with each other to form a ring, and in the formula (4), $R^5$ is an alkyl group having 1–2 carbon atoms, and wherein said distillation of the mixed solution is carried out in a distillation column having a column bottom temperature of not lower than 135° C. and a maximum concentration of said compound is maintained in the middle of the column.

2. The process according to claim 1 wherein the aliphatic saturated alcohol is selected from the group consisting of: ethyl alcohol, n-propyl alcohol, isopropyl alcohol, n-butyl alcohol, isobutyl alcohol, sec-butyl alcohol and tert-butyl alcohol.

3. The process according to claim 1 wherein the compound represented by the formula (3) is selected from the group consisting of: methyl ethyl ketone, methyl propyl ketone, 3-pentanone and methyl isobutyl ketone.

4. The process according to claim 1 wherein the step of distilling the mixed solution is carried out in the presence of 0.1–50 parts by weight of said compound per 100 parts by weight of propylene oxide in the mixed solution.

5. The process according to claim 1 wherein the step of distilling the mixed solution is carried out in the presence of 0.1–10 parts by weight of said compound per 100 parts by weight of propylene oxide.

6. The process according to claim 1 wherein the step of distilling the mixed solution is carried out in the presence of at least one compound selected from the group consisting of aliphatic saturated alcohols having 2–4 carbon atoms and allyl alcohol.

* * * * *